(12) United States Patent
Shemesh et al.

(10) Patent No.: US 7,980,998 B2
(45) Date of Patent: Jul. 19, 2011

(54) TRAINING AND INSTRUCTING SUPPORT DEVICE

(76) Inventors: Eldad Shemesh, Binymina (IL); Liat Shemesh-Granot, Binymina (IL)

( * ) Notice: Subject to any disclaimer, the term of this patent is extended or adjusted under 35 U.S.C. 154(b) by 96 days.

(21) Appl. No.: 12/382,214

(22) Filed: Mar. 11, 2009

(65) Prior Publication Data

US 2009/0239710 A1  Sep. 24, 2009

Related U.S. Application Data (63) Continuation-in-part of application No. PCT/IL2007/001121, filed on Sep. 11, 2007.

(60) Provisional application No. 60/843,422, filed on Sep. 11, 2006.

(51) Int. Cl.
A63B 71/00 (2006.01)

(52) U.S. Cl. ............ 482/8; 482/1; 482/9; 482/901

(58) Field of Classification Search ............ 482/1–9, 482/900–902; 434/247, 254; 702/182, 183; 705/2, 3
See application file for complete search history.

(56) References Cited

U.S. PATENT DOCUMENTS

| | | | |
|---|---|---|---|
| 4,301,808 A | 11/1981 | Taus | |
| 5,314,389 A | 5/1994 | Dotan | |
| 5,600,730 A | 2/1997 | Kenning et al. | |
| 5,685,722 A | 11/1997 | Taba | |
| 6,080,110 A | 6/2000 | Thorgersen | |
| 6,305,221 B1 | 10/2001 | Hutchings | |
| 6,955,542 B2 * | 10/2005 | Roncalez et al. | 434/254 |
| 7,670,263 B2 * | 3/2010 | Ellis et al. | 482/8 |
| 7,698,830 B2 * | 4/2010 | Townsend et al. | 33/512 |
| 2006/0136173 A1 * | 6/2006 | Case et al. | 702/182 |
| 2008/0004904 A1 * | 1/2008 | Tran | 705/2 |

FOREIGN PATENT DOCUMENTS

| | | |
|---|---|---|
| WO | WO 00/67858 A1 | 11/2000 |
| WO | WO 01/00281 A2 | 1/2001 |
| WO | WO 01/10508 A1 | 2/2001 |
| WO | WO 01/42809 A2 | 6/2001 |
| WO | WO 2004/038336 A1 | 5/2004 |

* cited by examiner

*Primary Examiner* — Glenn Richman
(74) *Attorney, Agent, or Firm* — The Nath Law Group; Susanne M. Hopkins; William L. Klima (57) ABSTRACT

A personal device is provided for measuring a training activity of a trainee having a body part which moves during this training activity, this movement at least partially defining said training activity. The device comprises a sensing unit adapted to repeatedly measure, during the training activity, parameters associated with the movement of the body part, and wherein the sensing unit comprising at least accelerometer means, a compass and, optimally, gyroscope means. The device further comprises means for attaching the sensing unit to the body part and a processor adapted to receive from the sensing unit the parameters and to calculate based thereon, data indicative of the training activity. In addition, there are provided a system for use by an instructor in instructing of a plurality of participants engaged in an activity, a communication system for communicating with one or more swimmers, the system comprising a transmitting module adapted to communicate in accordance with a wireless communication protocol with at least one receiving module associated with at least one swimmer, and a method for automated training one or more swimmers accordingly.

16 Claims, 9 Drawing Sheets

| Time | Measurements (Linear/Rotational) | Location S (x,y,z) | Orientation O (yaw,pitch,roll) |
|---|---|---|---|
| T1 | Ax1,Ay1,Az1 / Ayaw1,Apitch1,Aroll1 | Sx1,Sy1,Sz1 | Oyaw1,Opitch1,Oroll1 |
| T2 | Ax2,Ay2,Az2 / Ayaw2,Apitch2,Aroll2 | Sx2,Sy2,Sz2 | Oyaw2,Opitch2,Oroll2 |
| T3 | Ax1,Ay1,Az1 / Ayaw1,Apitch1,Aroll1 | Sx3,Sy3,Sz3 | Oyaw3,Opitch3,Oroll3 |

FIG. 4B

| Name | Number of completed finished laps | Elapsed time | Last lap time | Number of hand strokes per lap | Number of lag strokes per lap | Average distance per hand stroke | Heart bit rate | Average height of right hand stroke | Average height of left led stroke |
|---|---|---|---|---|---|---|---|---|---|
| Liat | 12 | 00:05:45 | 45 | 12 | 54 | 2.08 | 134 | 1.3 | 0.2 |
| Mulan | 32 | 00:20:45 | 35 | 14 | 65 | 1.79 | 142 | 1.2 | 0.15 |
| Yaeer | 11 | 00:06:12 | 54 | 15 | 88 | 1.67 | 145 | 1.1 | 0.1 |

FIG. 5

Swimmer name: Liat

| Lap number | Time per lap | Number of hand strokes | Number of lag strokes | Average distance per hand stroke | Heart bit rate | Height of right hand stroke | Height of left hand stroke | Number of right leg strokes | Number of left leg strokes |
|---|---|---|---|---|---|---|---|---|---|
| 1 | 45 | 12 | 45 | 1 | 120 | 2 | 2 | 45 | 45 |
| 2 | 32 | 13 | 46 | 2 | 121 | 2.2 | 2.2 | 46 | 46 |
| 3 | 28 | 14 | 47 | 3 | 122 | 1.9 | 1.9 | 47 | 47 |

FIG. 6

Swimmer Liat, Lap number: 35

| Time in the lap | Right hand height | Left hand height | Right leg height | Left leg height | Right hand orientation | Left hand orientation | Body orientation |
|---|---|---|---|---|---|---|---|
| 0.1 | 0.11 | -0.14 | 0.05 | -0.05 | 120 | 85 | 20 |
| 0.2 | 0.12 | -0.15 | 0.06 | -0.06 | 121 | 86 | 21 |
| 0.3 | 0.14 | -0.16 | 0.07 | -0.07 | 122 | 87 | 22 |

TRAINING AND INSTRUCTING SUPPORT DEVICE

This is a Continuation-In-Part of International PCT Application No. PCT/IL2007/001121 filed Sep. 11, 2007 and claims priority from U.S. Provisional Patent Application No. 60/843,422 filed Sep. 11, 2006, the contents of which are hereby incorporated by reference in their entirety.

FIELD OF THE INVENTION

The present invention relates to methods, systems and devices for monitoring activities performed by a person, and for allowing communication with respect thereto, in particular where such activities includes sports, e.g. swimming.

BACKGROUND OF THE INVENTION

Devices of the kind to which the present invention refers are disclosed for example in U.S. Pat. Nos. 5,685,722 and 5,600,730.

U.S. Pat. No. 5,685,722 is directed to goggles incorporating an electronic timer and display for displaying the times of a swimmer with a display accessible to a swimmer connected to the goggles. An accelerometer is used to determine a swimmer's movements with an electronic circuit for processing the information from the accelerometer to determine a swimmer's movements and time between movements.

U.S. Pat. No. 5,600,730 is directed to a swimming training device that may be part of an overall training system. The device is deployable releasably in a swimming cap and can receive electromagnetic wave signals. The device can then convert the signals into electrical charges which are then translated into audible sound. The system includes the cap with the receiving device and a transmitting source. The transmitting source allows the broadcasting of verbal instructions, as well as music and timing signals.

SUMMARY OF THE INVENTION

The present invention is directed to measuring movement parameters of a person who may be in individual or a member of a group, and who participates in an activity involving movement of at least one body part of the person, wherein the movement parameters may optionally be associated with the movement of said body part. For example, the measured movement parameters may be associated with the location and orientation of said body part of the person.

In at least some embodiments of the invention real-time communication is provided during said activity between an instructor and the person, in particular, a plurality of persons participating in such activity, and in case the activity is swimming, such communication may be of a swimming instructor with swimmers. When the activity is swimming, such instructor may be a trainer or a coach, and the participants may be trainees, for example. In general, the activity involving a group of participants and the instructor may be any suitable physical activity including a sport activity, in which participants are required to perform measurable body movements.

According to one aspect of the present invention, there is provided a system for use by an instructor in instructing of a plurality of participants engaged in an activity. The system comprises a plurality of personal measuring devices each adapted for being worn by one of the participants and for enabling repeated measurement, during the activity, of parameters relating to the participant's movements. The system includes a computer adapted for use by the instructor for wirelessly receiving from each of the personal measuring devices, data, which may be derived or calculated from the measured parameters, a monitor or other presentation means for presenting to the instructor the data or information derived therefrom, and optionally an input unit adapted to receive instructions from the instructor. In some embodiments, the instructor may only monitor the participants, and in other embodiments may also provide instructions to the participants using the input unit. The system may also include a plurality of presentation units, each for presenting to a participant at least the instructions of the instructor, and communication means connected to the computer and adapted to wirelessly transfer the instructions directly or indirectly to each of the presentation units.

Features of at least some embodiments of the system include that it allows the instructor to communicate with a plurality of participants during the activity, and to provide them with real-time instructions that are based upon measurements of their movement during the activity. Such instructions can be the same instructions for any group of the participants, or alternatively, the instructor can direct different instructions to different participants.

The system may also include any one of a plurality of different types of presentation units for enabling the participant to receive the instructions. One type of such a unit may be a screen adapted to be worn by each of the participants, e.g. on his/her wrist, or a screen that is visible elsewhere to the participants. Another type of the presentation unit may be earphones to be worn by each participant. The earphones may be connected to a receiving module adapted for wirelessly receiving the instructions, or any other communications, in digital format, and converting them into audio signals to be transmitted to the participant via the earphones.

The computer that is operated by the instructor, can also process and analyze the data received from the participants' personal measuring devices in order to provide various information and statistics to the instructor. For example, such information may include comparative data regarding various participants that are engaged in the activity. As for the personal measurement devices, such devices may each include a sensing unit adapted to repeatedly measure, during the activity, parameters characterizing movement of a specific body part of a single participant, for example, the location and orientation of this body part relative to its initial position and orientation, or to any other predefined position and orientation, and means adapted for the attachment of the measuring device to this specific body part. In this embodiment, the measuring device may further include a processor adapted to receive from the sensing unit the measured parameters, and to calculate, based thereon, information indicative of the participant's activity, which includes the location and orientation of the body part for each of the measurements.

According to another aspect of the present invention, there is provided a communication system particularly suitable for the communication with one or more swimmers. The system comprises a transmitting module adapted to communicate in accordance with a wireless communication protocol with at least one receiving module associated with at least one swimmer. The transmitting module is adapted to obtain data designated to at least one swimmer, to accommodate the data and/or derivatives thereof thus giving rise to accommodated data, to process the accommodated data in order to fit it to the wireless communication protocol, and to transmit the processed data to the at least one receiving module upon a predefined condition. The receiving module which is associated with at least one swimmer is adapted to receive the data transmitted from the transmitting module and process it in order to facilitate presenting it to the swimmer. The predefined condition may be communication availability of the at least one receiving module and the wireless communication protocol may be configured to recognize the communication availability of the at least one receiving module.

The data may be originated from an audio signal and the transmitting module may further be adapted to convert the audio signal into the data. The audio signal and/or the data, may be associated with instructions from an instructor.

The process of accommodating the data in the transmitting module may include compressing the data, and the process in the at least one receiving module may include decompressing the data. The communication protocol may be a Bluetooth protocol.

In case the communication system is designed for communication with a swimmer, the receiving module may constitute a part of a device attachable to the wrist of the swimmer and/or a part of a device attachable to the head of the swimmer. In the latter case, the receiving module may additionally comprise at least one earphone and may be adapted for converting the data into audio signal to be transmitted to the swimmer via the at least one earphone. The receiving module may also include digital media means adapted to display music to the swimmer via the at least one earphone. Alternatively or additionally, the receiving module may include a screen that is adapted to facilitate presenting of data to the swimmer. Moreover, the receiving module may be adapted to further transmit the data to an additional receiving module which may constitute a part of an additional device which may be attached to the head of the swimmer. The additional device may thus comprise at least one earphone and may be adapted for converting the data into audio signal to be transmitted to the swimmer via the at least one earphone.

According to yet another aspect of the present invention a method for automated training one or more swimmers is provided. The method comprises:
  (a) obtaining data related to one or more training instructions designated to at least one swimmer among the swimmers;
  (b) automated processing the obtained data in order to fit a wireless communication protocol; and
  (c) transmitting the processed data to at least one receiving module associated with the at least one swimmer upon a predefined condition; wherein the predefined condition is communication availability of the at least one receiving module, and the wireless communication protocol is configured to recognize the communication availability of the at least one receiving module.

The method may also include receiving the transmitted data and further processing thereof in order to facilitate presenting the data related to training instructions to the at least one swimmer.

The automated processing of the obtained data may additionally comprise a compression operation and processing the received data may further comprise a decompression operation.

Among advantages of the communication system and method of training in accordance with certain embodiments of the present invention is facilitating successful communication of certain data (e.g. training instructions, music, etc.) to a designated swimmer, or a group of such swimmers, during swimming, despite the inherent physical communication barriers that exist when the swimmers are submerged during swimming and other underwater activities.

According to yet another aspect the present invention, a personal device for measuring a training activity of a trainee, is provided. Such a device is adapted to measure parameters associated with the movement of a body part of the trainee during the training activity, and comprises a sensing unit which includes accelerometer means, a compass, and optional gyroscope means, means for attaching the sensing unit to the body part, and a processor adapted to receive from the sensing unit said parameters, and to calculate, based thereon, data indicative of the training activity.

As the body part may change its location and orientation during the training activity, the parameters may characterize the location and orientation of the body part relative to its initial position and orientation, or to any predefined location and orientation, and the data may accordingly include at least the location and orientation of the body part for each of the measurements.

The personal device allows to determine, and later present, the exact location and orientation of the body part of a trainee, based on which the trainee or the instructor may reach conclusions regarding various characteristics of the trainee's movement, and by this, may help the trainee to improve his/her movements and subsequently his/her abilities.

The accelerometer means may be adapted to measure linear acceleration of the body part along three axes and the gyroscope means may be adapted to measure angular acceleration of said body part around said three axes, by virtue of which the parameters may be at least linear and angular acceleration values.

The device is particularly useful for automatic measuring repetitive activity, in which case said processor may be adapted to calculate the periodicity of said activity based on parameters received from the sensing unit.

In at least some embodiments of the invention, the means for attaching the sensing unit further comprise a flexible platform adapted to amplify at least one of the measurements obtained from the sending unit(s).

Optionally, the device may comprise more than a single sensing unit, wherein each sensing unit will be attached to a different body part of the trainee, such as for example, to any of his/her limbs, his/her head, or his/her waist. This may allow simultaneous measurement of parameters characterizing the location and orientation of the additional body part of the trainee relative to its initial location and orientation. In this case, the processor may be further adapted to receive the measured parameters from all the sensing units and, based thereon, to calculate, for each measurement, at least the location and orientation of all the body parts whose movements are measured.

The data which is calculated by means of the device, may be further processed, and/or stored for later usage, and/or presented to the trainee and/or to others in various ways, and/or transmitted to an external computer for different purposes in real-time. It will be appreciated that many different options of such usage are possible. A memory unit may further be included in the device for storing the data, optionally for later usage, and the processor may be configured for exporting the stored data to a computer to be displayed or further analyzed. Further optionally, the data may be exported to and internet/intranet network, where it may be shared with other users of similar devices.

Optionally, the data may further include statistics and summary results for any specific activity, and wherein the activity is swimming, the data may relate, for example, to statistics and summary results for swimming sessions or laps. For example, the results may include one or more of the following: total training time, number of laps, average lap time, average lap velocity, average strokes per lap, fastest and slowest lap, highest and lowest number of hand strokes per lap, instantaneous speed during the laps, hand or leg lifting height for each stroke, distance traveled for each stroke, comparative results to other trainees using similar devices.

Further, optionally, the device may comprise a pulse measuring unit adapted for being held in contact with the trainee during said activity, in which case the data provided by the measuring device may also include the pulse rate of the trainee. Said pulse measuring unit may be of an IR type, and include an infrared emitter and a corresponding infrared sensor. In the present invention, the pulse measuring unit may be adapted to both measure the pulse and audibly present the results simultaneously in at least one ear canal and with a single earphone. Optionally, the unit may measure the pulse and play the results together with any other audio information (i.e. music, instruction) simultaneously in both ears.

Moreover, the device may be designed to eliminate the adverse effect on the pulse measurement of sudden movements of the trainee (or any part of his/her body) during the activity. This goal is achieved by using sensing devices such as accelerometers. The sensors may have a waterproof design or the device may including sealing means for their sealing to allow the use of these sensors even when the trainee is submerged in water.

Another type of data which may be produced by the processor of the measuring device and displayed, is a graphic illustration of the trainee or of any of his/her body parts whose movement is measured in various moving positions, or as a video simulation that is displaying such movement in real-time. It will be appreciated by a person skilled in the art that the processor may calculate further types of data that may be derived from any of the measurements and from any combination thereof. It will also be appreciated by a person skilled in the art that any additional information which is known in the art may be included in that data, for use in further calculations, displaying, or otherwise.

The personal measuring device may be part of a training advisor system that may involve providing the trainee with instructions which are based, objectively or subjectively, upon the measurements, and the measuring device may include a presentation unit for the trainee. One possible option for such a unit is a viewing screen which is connected to the processor. This option may be applicable, for example, when the device is attached to a body part that is visible to the trainee, for example, to his/her wrist. Another option of presenting the data to the trainee is using earphones. The earphones may be connected to a receiving module adapted for wirelessly receiving the data, or any other communication, in digital format, and converting it into audio signal to be transmitted to the trainee. Alternatively, a single earphone may be used. It will be appreciated that the data can be presented to the trainee in real-time, i.e. in the course of the activity and during the corresponding measurements. Yet another option is to use a mechanism for providing signals that are configured to be felt by the trainee, and such a mechanism may comprise, for example, a vibrating element designed to generate vibratory pulses and direct these to the skin of the trainee.

The source of the instructions presented to the trainee may also vary. One option is for the processor itself to be adapted to automatically provide instructions according to predetermined rules and based upon the data that it calculates from the measured parameters. Such an option may be implied also on a remote computer that wirelessly receives the data from the device, and provides instructions in a similar manner to be transmitted back to the trainee. Alternatively, a user of the computer, which for example can be a trainer, may observe the data on a monitor, and may provide instructions using an input device, for example a keyboard or a microphone, to be transmitted back to the trainee. The last two options are for the computer to be adapted to wirelessly transfer the instructions directly or indirectly to the presentation unit.

The training advisor may constitute a part of a training system comprising a plurality of such training advisors for a corresponding plurality of trainees, wherein the presentation unit that is used by the trainer is adapted to present to him/her data or information derived therefrom and relating to those plurality of trainees. Such a system may also be adapted to present to the user the data or information, in a real-time activity of the plurality of trainees, and may also allow the computer to simultaneously and wirelessly transfer the instructions of its user directly or indirectly to each of the plurality of trainees, or a group thereof, upon the user's choice. Optionally, when the activity is swimming, the communication with the trainees, i.e. swimmers, may be preformed with the devices and/or methods which described below.

BRIEF DESCRIPTION OF THE DRAWINGS

In order to understand the invention and to see how it may be carried out in practice, embodiments will now be described, by way of non-limiting examples only, with reference to the accompanying drawings, in which.

DETAILED DESCRIPTION OF EMBODIMENTS

In the following detailed description, numerous specific details are set forth in order to provide a thorough understanding of the invention. However, it will be understood by those skilled in the art that the present invention may be practiced without these specific details. In other instances, well-known methods, procedures, components and circuits have not been described in detail so as not to obscure the present invention.

Unless specifically stated otherwise, as apparent from the following discussions, it is appreciated that throughout the specification discussions, utilizing terms such as, "processing", "computing", "calculating", or the like, refer to the action and/or processes of a computer or computing system, or processor or similar electronic computing device, that manipulate and/or transform data represented as physical, such as electronic, quantities within the computing system's registers and/or memories into other data, similarly represented as physical quantities within the computing system's memories, registers or other such information storage, transmission or display devices.

Embodiments of the present invention may use terms such as, processor, computer, apparatus, system, sub-system, module, unit, device (in single or plural form) for performing the operations herein. This may be specially constructed for the desired purposes, or it may comprise a general purpose computer selectively activated or reconfigured by a computer program stored in the computer. Such a computer program may be stored in a computer readable storage medium, such as, but not limited to, any type of disk including optical disks, CD-ROMs, magnetic-optical disks, read-only memories (ROMs), random access memories (RAMs), electrically programmable read-only memories (EPROMs), electrically erasable and programmable read only memories (EEPROMs), magnetic or optical cards, any other type of media suitable for storing electronic instructions that are capable of being conveyed via a computer system bus.

The processes/devices (or counterpart terms specified above) and displays presented herein are not inherently related to any particular computer or other apparatus, unless specifically stated otherwise. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

Figure 1:
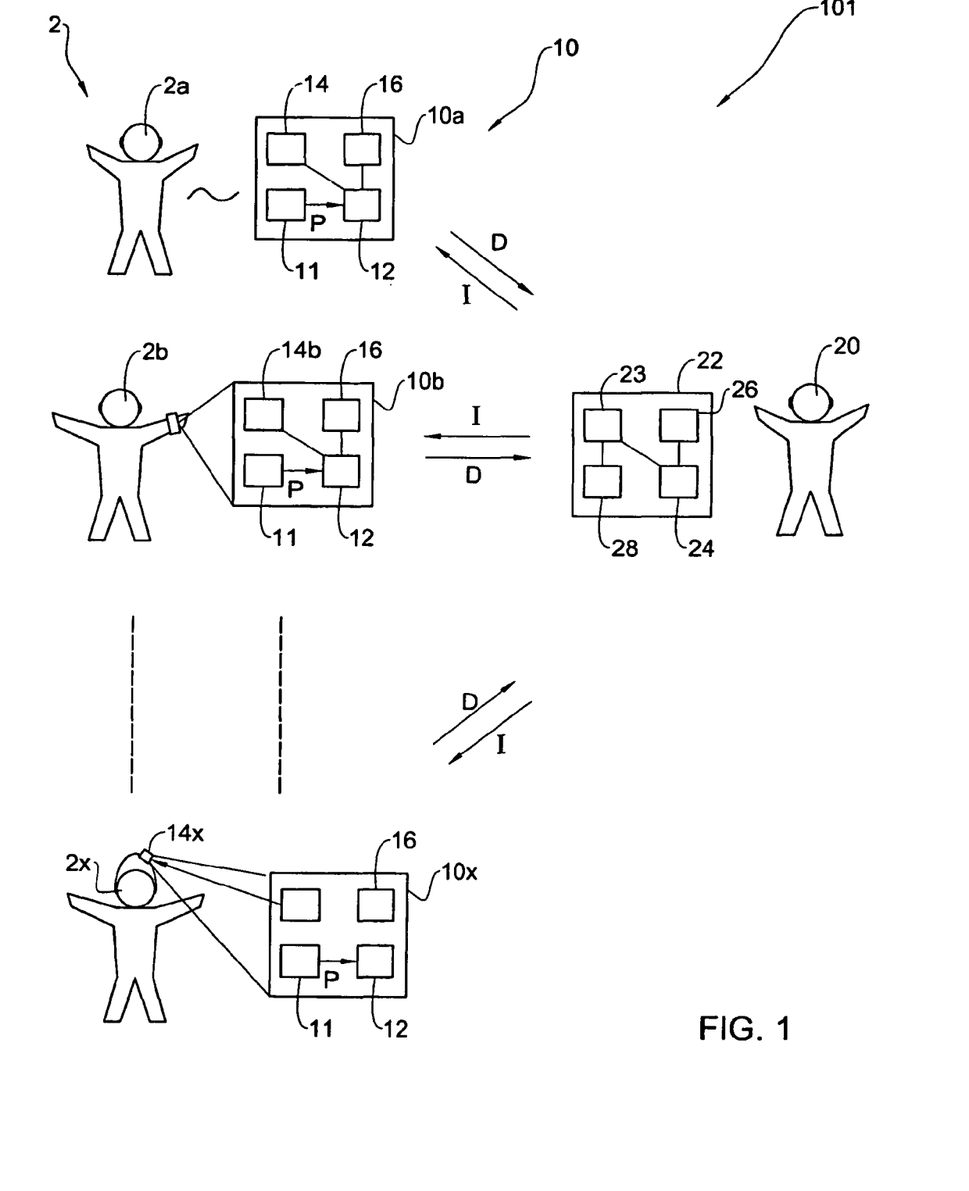
FIG. 1 is a block diagram of a training advising system according to one embodiment of the present invention.

Referring to FIG. 1, a block diagram of a training advising system according to a first embodiment of the invention, generally designated with numerals 101 is adapted for use by an instructor 20 in instructing a plurality of participants 2 engaged in an activity according to one example of the present invention. The activity may be, for example, any sport activity, for example swimming, as well as other activities which involve physical activity of plurality of participant and an instructor, particularly such an activity in which the instructor 20 may monitor and, optionally instruct, the participants 2 in real time. According to aspects of the invention, the participants 2 may include sportsmen, trainees and so on, for example, and/or the instructor 20 may include a teacher, coach, trainer, and so on.

The system 101 comprises a plurality of personal measuring devices 10a, 10b, . . . 10x, which may be substantially identical, and which for ease of reference may each be referred to as device 10. Each device 10 is adapted for being attached to a corresponding one of the participants 2a, 2b, . . . 2x, which for ease of reference may each be referred to as participant 2. Each device 10 is also adapted for enabling any parameter(s) P related to the participant's movement to be measured repeatedly for a time period during the activity, and comprises a sensing unit 11 that is adapted to measure any such parameter(s) P, as will be further detailed below. Each device 10 may further comprise an amplifier (not shown) adapted to amplify at least one of the measurements obtained from the sending unit. Each device 10 may further comprise measuring units for measuring health condition parameters of participant 2, such as pulse rate or ECG measuring units (not shown) Each device 10 also comprises a processor 12 that is operatively connected to the corresponding sensing unit 11 and can derive, calculate or otherwise determine various data D from the measured parameters P. Each personal device 10 also comprises a presentation unit 14 that is adapted to present information, including these various data D, and also instructions I (if exist) sent from the instructor 20 to the participant (s) 2. Presentation unit 14 may include, for example, an audio generation system, and/or a video generation system and/or any other presentation means that enable the desired information to be presented to the corresponding participant 2, as will be further detailed below. The presentation may be done in real-time, and during the activity, as well as after the activity as post-activity briefing which is useful for self training for example. In such embodiment (not shown) a memory component is desired in order to accommodate the parameters P and/or data D and a wireless communication module is not necessary.

In addition, each of the personal devices 10 comprises a communication module 16 adapted to wirelessly transmit the data D, which can also include the original parameters P, to enable the same to be presented to instructor 20. Communication module 16 may apply any wireless communication technology. Such technology may include, for example, a Blue Tooth protocol, ZigBee protocol and Wi-Fi technology.

The personal measuring device 10 according to one example of the invention, may be adapted for being worn by the corresponding participant 2, directly on the body, for example on the wrist, in a similar manner to a watch, for example, or on the upper arm in a likewise similar manner, or, in other examples, can be adapted to be attached to a headband, goggles, shoes, wet socks or any other clothing or accessories or other means which are inherently attached to or worn by the participant. For example, and referring to FIG. 2A, each device 10 may be encapsulated in a suitable housing 60, which according to the particular activity may be water proof, dust proof, weather proof, heat proof, and so on, and may optionally include an interface 62 for direct or indirect attachment to the participant 2, in particular with respect to a desired particular body part thereof. For example, the interface 62 may comprise an elastic and/or adjustable band, for wrapping around the wrist, upper arm, forearm, waist, ankle, head, thigh, calf, and so on; alternatively, the interface 62, may comprise a clamp or the like, or a Velcro patch, adhesive patch or any other suitable means for clamping or otherwise attaching the device 10 onto an armband, waistband, belt, pocket, goggles, cap, and so on. Alternatively, a pocket, strap or other restraining enclosure on a suitable item of clothing or accessory, for example worn by or attached to the particular body part of the participant, at least during the activity, may be provided for accommodating the device 10.

The means for attaching the measuring device or its sensing unit may incorporate therein the amplifier mentioned above, adapted to amplify at least one of the measurements obtained from the sending unit. For example, the amplifier may be in the form of a flexible platform which, when located on a moving part of the user's body, such as for example, the wrist of a swimmer, amplifies the reading from the sensing unit in each movement of said part, e.g. on each hand stroke of the swimmer.

Alternatively, the various components of the device 10, for example sensing unit 11, presentation unit 14, communication module 16 and so on may each be comprised in a separate housing and attached to a different body part of the participant 2, the various components being operatively interconnected for example via wires, optic cable, wireless communication, and so on.

The system 101 further comprises a computer 22, for example a pocket PC, laptop, palm device, Desktop computer, and so on, adapted for use by the instructor 20 during the activity of the participants 2. The computer 22 comprises another communication module 28 which adapted to communicate with the communication module 16, e.g. for wirelessly receiving from each of the personal measuring devices 10, the data D generated by each device 10. The computer 22, having a processor 23, can be adapted for suitable manipulating the data D from each device, and for example perform suitable calculations to provide further information based on the data D. The computer 22 is operatively connected to a monitor 26, or alternatively to a printer or other display to display to the instructor 20 any part of the data D or the information derived therefrom which the instructor 2 chooses to view. It will be noted the instructor may choose to view data concerning either one of the participants 2, or any group of participants 2 at any one time, and may selectively switch viewing between participants or groups thereof as desired. The computer 22 also has a user interface including input 10 unit 24, which can be, for example a keyboard, a microphone, tablet, touch screen or any other device capable of enabling instructions I from the instructor 20 to be received into computer 22. The instructions I can be re-directed to any one of the participants 2, and/or to any group of participants 2, and accordingly, the computer 22 is configured to wirelessly transmit via its communication module 28 the instructions I to one or more of the corresponding participants 2 as designated by the instructor 20. The instructions I received by each of the corresponding participants 2 are presented thereto via the corresponding presentation units. An example of the operation of the system 101 is provided below.

The source of the instructions I and the manner in which such instructions may be generated may vary according to the particular application of system 101. In some embodiments, the instructor 20 manually inputs instructions to be sent to one or more participants via computer 22, or may choose instructions from a menu provided in the computer. Alternatively, and, for example, in other embodiments of the invention, any of the processors 12 and/or 23 may be adapted to automatically provide instructions I according to predetermined rules and based upon the data D provided by the device(s) 10, i.e., without the need of an actual trainer or instructor 20 to actively provide such instructions, and hence in this example the system may be referred to as a "Virtual Training" system. In yet other applications of the system 101, the instructions I are generated only by the processor 12, and for such variations of the first embodiment of the invention there is then also no need for an additional computer 22 or for communicating the data D externally with respect to the device 10.

An example of a predetermined rule may correspond to: "if the height of the right hand stroke is greater than X mm—display to the swimmer instruction to lower his/her right hand strokes". In such an example, the device 10 monitors parameters P such as to be able to determine or to directly provide at least the height of the right hand stroke of the participant—if during such monitoring, which may include sampling and/or determining this height as often as is desired or predetermined according to preset rules, the height of the right hand stroke is greater than X mm, the processor 12 (or the computer 22) will thus generate a signal or command that will cause the display unit to transmit a message meaning "lower right hand stroke" to the user. The message may be a visual text message, a corresponding image, a suitable audio verbal message or signal, and so, in a manner that will be understood by the particular participant, who is nominally previously trained to understand such messages when the message is not a verbal or textual message, and as will be further detailed below.

Those skilled in the art will readily appreciate that the invention is not bound by the configuration of FIG. 1; equivalent and/or modified functionality may be consolidated or divided in another manner and may be implemented in any combination of software, firmware and hardware.

The Sensing Unit

A more detailed description will be given now to the sensing unit 11. As discussed above, the measuring device 10, which comprises sensing unit 11, is adapted to be attached 10 to each of the participants 2, and the sensing unit 11 is configured to measure, during the activity, one or more parameters P that characterize the movement of the corresponding participant 2 relative to his/her initial location and orientation or any other datum location and orientation for that matter.

Figure 2A:
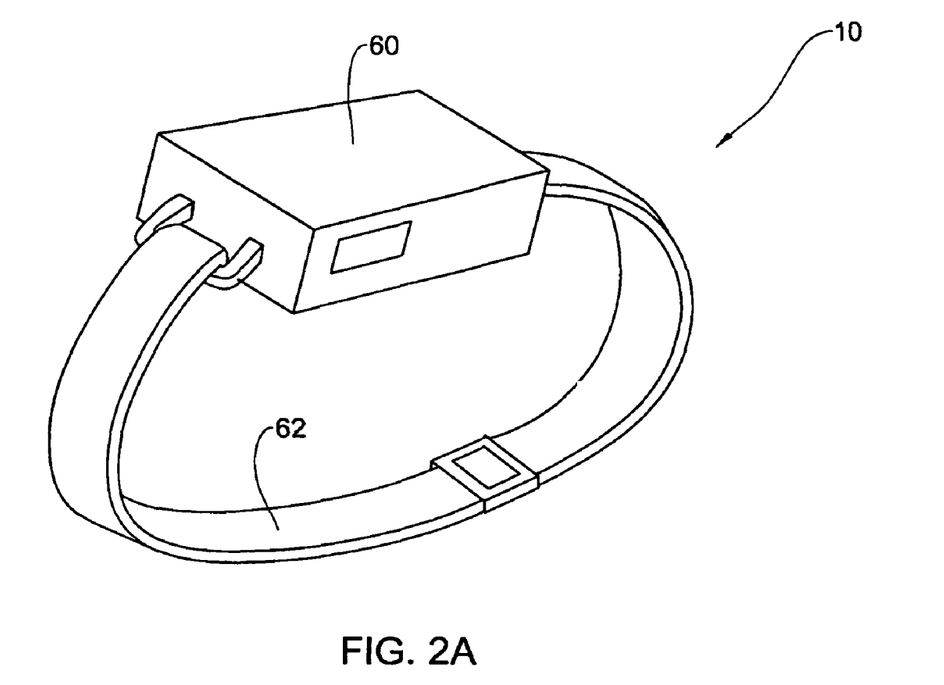
FIG. 2A is an illustration of a personal measuring device according to another embodiment of the invention.
Figure 2B:
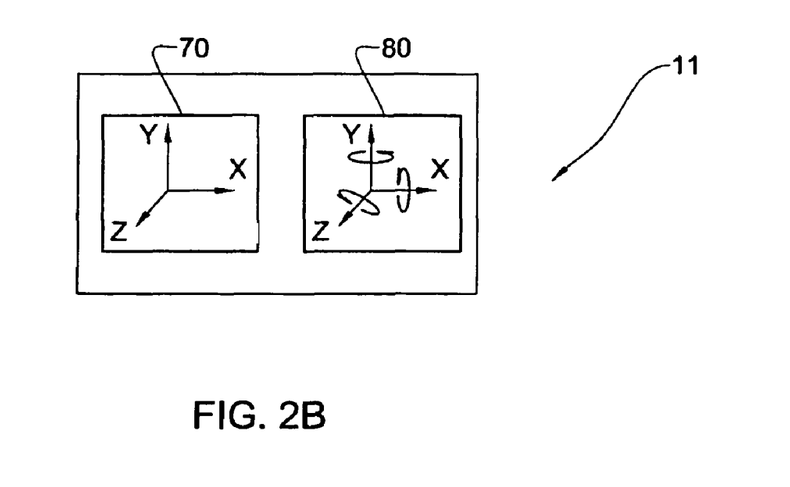
FIG. 2B is a schematic illustration of a sensing unit in a personal measuring device of FIG. 2A.

Additional reference is made now to FIG. 2B which is a schematic illustration of a sensing unit according to one example of the invention. In this example, sensing unit 11 is adapted to be attached (integrally with the personal measuring device 10) to a specific body part of the participant 2, and it is designated to measure, during the activity, parameters P that characterize the movement of the corresponding body part relative to its initial location and orientation.

The sensing unit 11 may comprise accelerometers, gyroscopes, compasses or any combination thereof. When the measuring device 10 is designed for swimming activity, the device may comprise sealing the sensing unit, or at least each device used therein and requiring such sealing, in a way that will allow its use even when the participant 2 is submerged in water.

In the shown example, the sensing unit 11 comprises an arrangement to determine the movement of the body part along six degrees of freedom, and includes an accelerometer module 70 adapted to measure linear acceleration of the measured body part along three orthogonal axes, and a gyroscope module 80 adapted to measure angular acceleration of the body part around the three orthogonal axes, i.e, with respect to yaw, pitch and roll. Thus, the parameters P which are provided to the processor 12, in this example, include at least linear and angular acceleration values with respect to the three orthogonal axes, X, Y and Z.

In repetitive activity, the sensing unit may be adapted to measure the periodicity of such activity. For example, in a swimming activity, accelerometers periodicity is easy to find outside of water due to the high readings obtained when the user hitting the ground.

In some embodiments, the sensing unit 11 may be placed at approximately the center of gravity of the participant 2, and may be used to monitor the movement of the participant 2, rather than of a body part thereof.

In other example, a compass (not shown) may be used whose advantage is in that its measurements are provided relative to the earth electromagnetic field as an external reference point (outside the sensor). For applications of the kind described above, the compass may be three dimensional and it may be, for example, located on the head of the user, and be able, for example, to reveal if the user stands or lays down on the ground, as well as the changes in the direction of movement of the user (or any part of his body) such as a turn in a swimming pool (at the end of each lap, for example).

Figure 3:
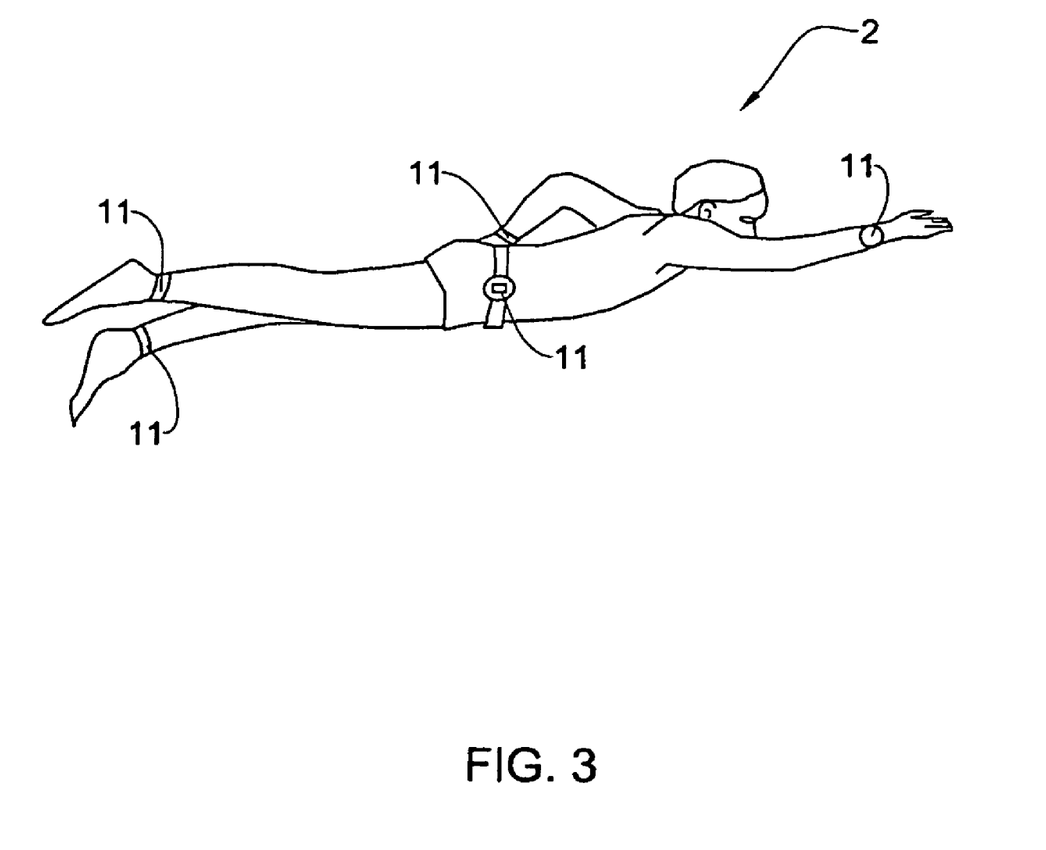
FIG. 3 is an illustration of a swimmer wearing sensors on his/her limbs according to an embodiment of the invention.

In variations of the first embodiment, each device 10 may comprise more than a single sensing unit 11 wherein each sensing unit may be attached to a different body part of the participant 2, such as for example, on any part of the limbs, head, or waist. For example, as can be seen in FIG. 3, a swimmer participant 2, may be equipped with five sensing units 11 on his limbs and torso, in particular one sensing unit 11 being worn on each of the two wrists, the two ankles and the waist, according to one embodiment of the invention. This embodiment may allow simultaneously measurement of parameters characterizing the location and orientation of a plurality of body parts of the participant relative to their respective initial locations and orientations. In this embodiment each sensing unit 11 may be interconnected for example via wires, optic cable, wireless communication to a single measuring device, or alternatively, each sensing unit may constitute a part of a separate device 10, as a single participant 2 may, in an alternative embodiment of the invention, concurrently use more than a single device.

Figure 4A:
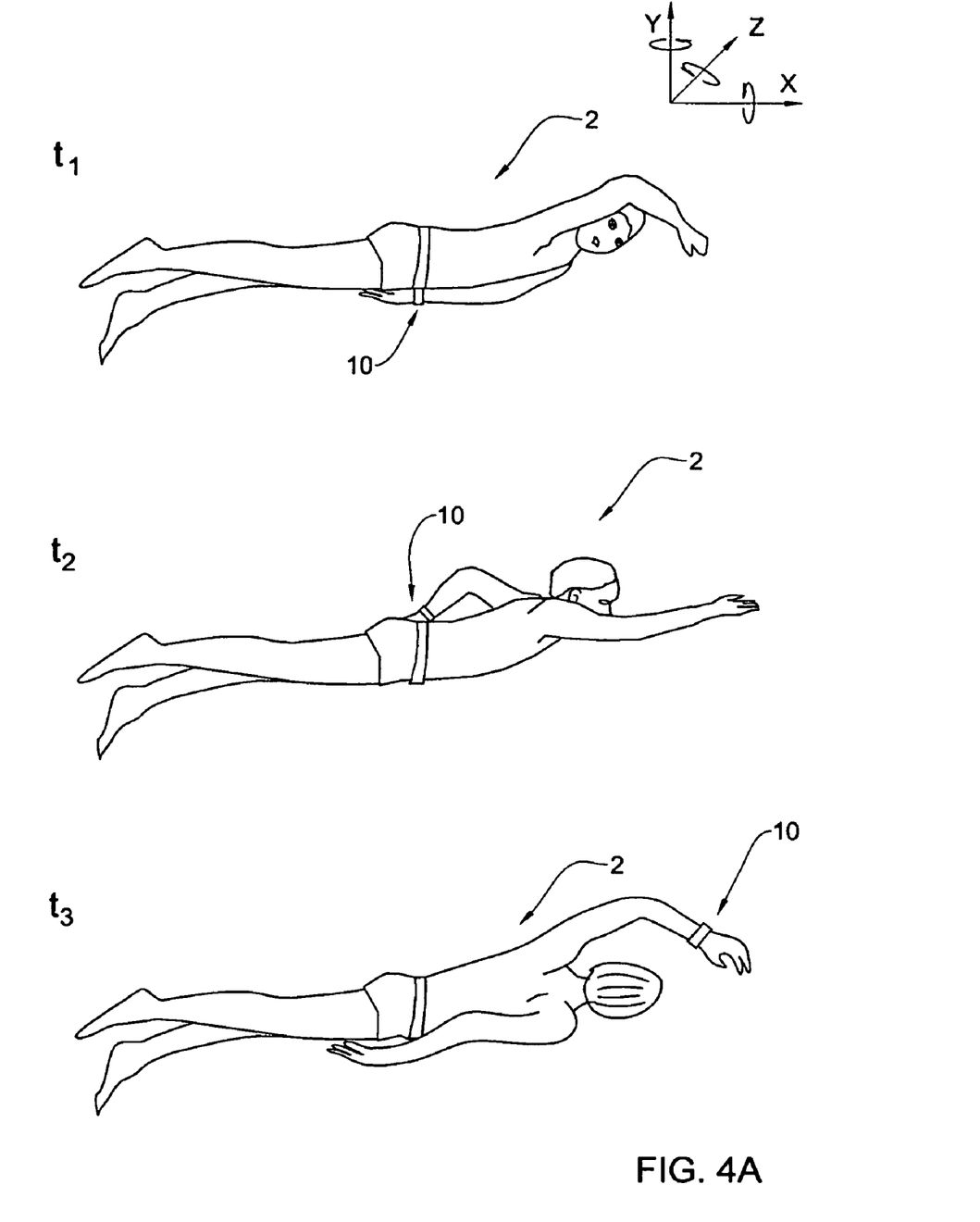
FIG. 4A illustrates one example of a swimmer in three different states, using the sensing unit as illustrated in FIG. 2.

As for the operation of the illustrated sensing unit 11 as part of a system according to one embodiment of the present invention, reference is also made now to FIGS. 2A and 2B as well as to FIG. 4A which illustrates an example including a participant 2 while performing a swimming activity (freestyle) and using a personal measuring device 10 attached to his left wrist and having a sensing unit 11 comprised therein.

Figure 4B:
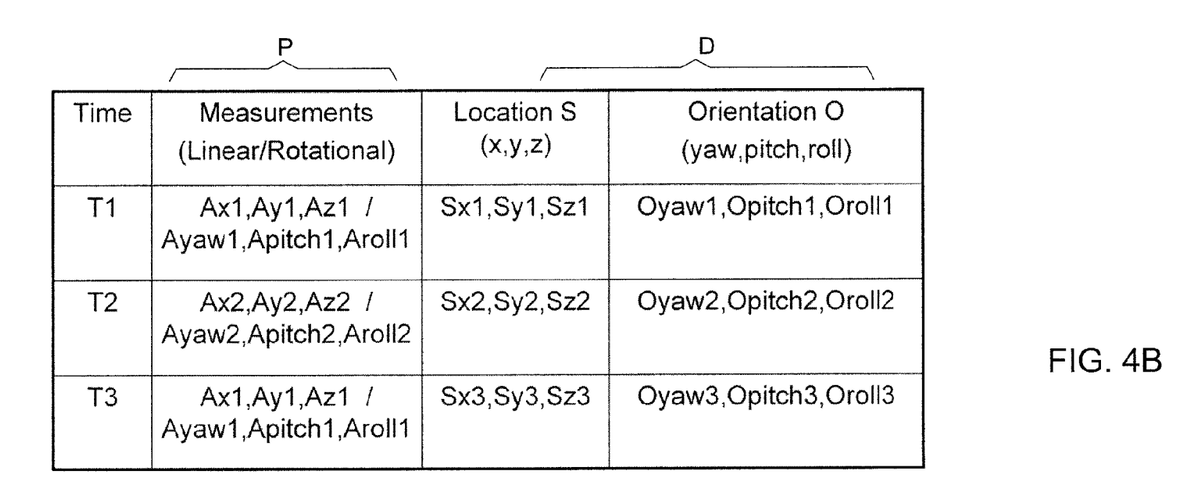
FIG. 4B is a table which includes examples of parameters and calculated data for each measurement taken by the sensing unit in the example in FIG. 4A.

While swimming, the sensing unit 11, in this example, repeatedly samples linear and angular acceleration values of the left wrist. According to those values, the processor 12 calculates for each reading the location and orientation of the left wrist of the swimmer. The frequency of the sampling of the sensing unit is predefined and can be adapted, for example, to different types of activities. In FIG. 4A, three different consecutive positions of the swimmer participant 2 are illustrated and referred to as t-1, t-2 and t-3. In each of said positions, the wrist of swimmer participant 2 changes its location and orientation, and for each position sensing unit 11 samples linear and angular acceleration values (which constitute parameters P) and the processor 12 calculates the location and orientation of the wrist (which constitute data D). Reference is made now to FIG. 4B that includes a table which details the parameters P and the calculated data D for each of the measurements in t-1, t-2 and t-3 of the present example.

The data D provided by the processor 12, which in this example constitutes the location and orientation of the body part being monitored for any given period of time, may be further processed (as will be described below in detail when discussing the operation of the computer 22) and/or stored within device 10 within a memory unit (not shown) for later use. In such a use, for example, the participant 2 can transfer such stored data to a computer after he finishes his activity for an ex-post study and analyzing his/her activity, for this function, while the processor 12 may have the capability to export the stored data D (many export alternatives are available in the art). In such embodiment wireless communication means are not necessary.

The data D can be also be presented to the participant 2 by the presentation unit 14 in real-time. Optionally, the data D may be transmitted via wireless communication module 16, in real-time, to an external computer 22. Further optionally, the data may be exported to and internet/intranet network, where it may be shared with other users of similar devices. It will be appreciated that more than a single option of such usage is possible for a single device.

Pulse Rate Measuring Unit

Pulse rate measuring unit (not shown) may be provided for measuring the pulse rate of the participant 2. The pulse measuring unit (PMU) may be adapted for being held in contact with the participant during his activity with or without connection to a measuring device 10.

The PMU may be in the form of an external non-invasive detector adapted to measure the pulse rate in the participant's ear or other thin appendage of his body. One type of such detector is disclosed, for example, in U.S. Pat. No. 5,314,389, where it is used in an electrocardiograph (ECG). Another type is a technique using IR technology, comprised of an infrared emitter and a corresponding infrared sensor, as disclosed for example in U.S. Pat. Nos. 4,301,808 and 6,080,110, whose description from these references and the manner of operation are incorporated herein by reference. According to this technology, the emitter and the sensor are attached to the one user's ear so as measure the pulse inside that ear and play the results together with music via a headset to the other ear.

In the measuring device 10, the PMU may be adapted to measure the pulse and audibly play the results simultaneously in at least one ear canal and with a single earphone. Optionally, the device may measure the pulse and play the results together with any other audio information (i.e. music, instruction) simultaneously in both ears.

Moreover, in some embodiments of the present invention, the device may be designed to eliminate the adverse effect on the pulse measurement of sudden movements of the participant (or any part of his body) during the activity. This goal is achieved by using sensing devices such as accelerometers.

When the measuring device 10 is designed for swimming activity, the device may comprise sealing the above PMU, or at least its emitter and sensor, in a way that will allow its use even when user is submerged in water.

The Computer

A more detailed description will be given now regarding the computer 22. The computer 22, can additionally process the data D received from each of the participants 2 in order to provide information including statistical information regarding one or more participants, which the instructor 20 may choose and display via monitor 26. For example, such information may include comparative data regarding various participants 2 (or any group therefrom) that are engaged in the activity, their summary results and various statistics.

Wherein the activity is swimming, the data may relate to statistics and summary results for swimming sessions or laps. More particularly, the results may include one or more of the following: total training time, number of laps, average lap time, average lap velocity, average strokes per lap, fastest and slowest lap, highest and lowest number of hand strokes per lap, instantaneous speed during the laps, hand or leg lifting height for each stroke, distance traveled for each stroke, comparative results to other participants using similar devices.

Another type of data which may be generated by the computer 22 and displayed is a graphic illustration of the participant or of any of the measured body parts thereof in various moving positions, or as a video simulation that is displaying such movements in real-time. It will be appreciated by a person skilled in the art that the processor may calculate further types of data that may be derived from any of the measurements and from any combination thereof. It will also be appreciated by a person skilled in the art that any additional information which is known in the art may be included in that data which is either used for further calculations, displaying, or otherwise.

Although that in the example which is illustrated in FIG. 1 a plurality of participants 2 and an instructor 20 having a computer 22 are presented, it would be appreciated, that the additional processing and analyzing described herein may be performed in other embodiments by the processor 12 of the device 10 instead of, or in addition to, the processor 23. In particular, such processing and analysis may be performed in yet other embodiments, by the participant himself after finishing the activity as was described above, and retrieving the data from the memory.

Figure 5:
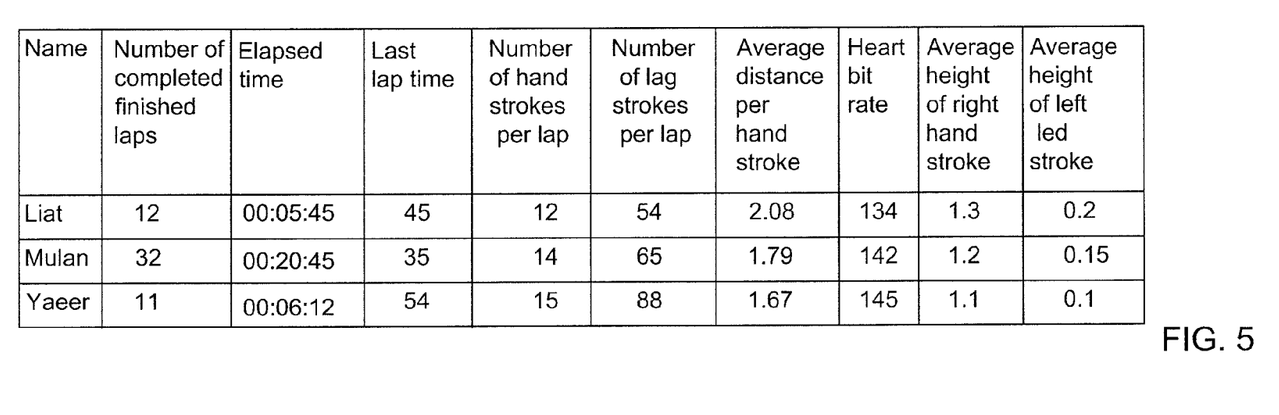
FIGS. 5-7 illustrate examples of various possible screen shots that a trainer may choose to observe during a swimming activity when using an advising system according one embodiment of the present invention.
Figure 6:
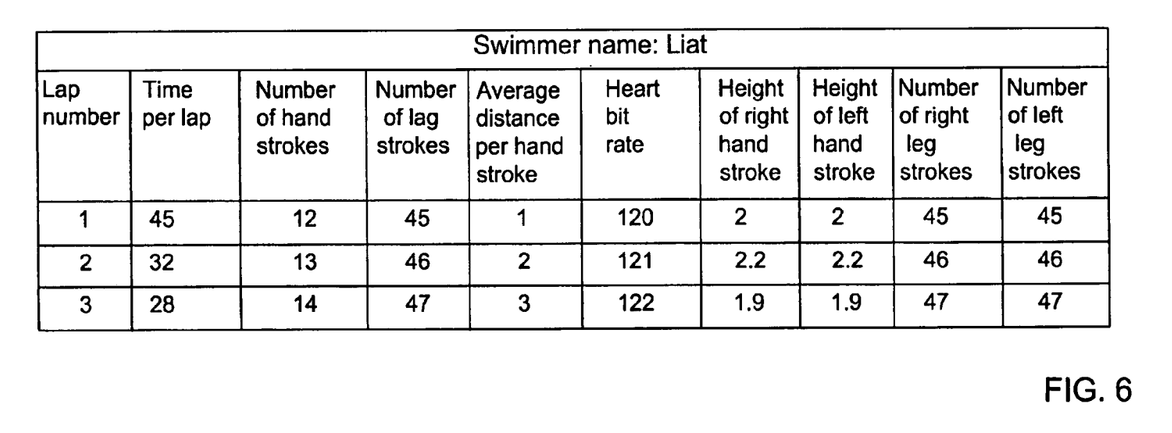
Figure 7:
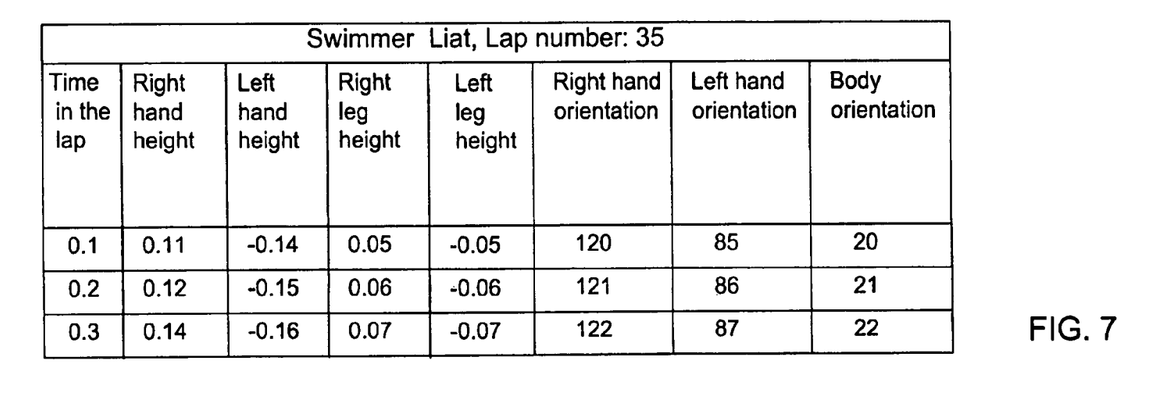

FIGS. 5 to 7 are schematic examples of various possible screen visual displays that a trainer instructor may choose to view during a swimming activity of three swimmer participants, who are referred to therein as: Liat, Mulan and Yaeer. As can be appreciated, there are various alternative viewing configurations for the data relating to the swimmer participants. For example, comparative information regarding several swimmers may be presented and viewed simultaneously (FIG. 5); detailed information may be viewed regarding an activity in real time of a single swimmer (FIG. 6) or even during a single lap (FIG. 7).

The Presentation Unit

A more detailed description will be given now to the presentation unit 14 with reference to FIG. 1. The system 101 may include different types of presentation units 14 for enabling any of the participants 2 to receive instructions I and/or data D.

For example, in one personal measuring device 10b, the presentation unit may be visually based, and includes a screen 14b which constitutes a part of the device 10b being worn by participant 2b. In such embodiment, the screen (with the device) should be located at a position which will enable the participant to see it during the activity and according to it. In another example (not shown) which is relevant for swimming or any other activity which involves wearing goggles or a helmet (i.e. American football, ski), a screen may be a part of goggles that may present data as well as enable the wearer, at the same time, to look ahead.

Another example of a presentation unit is used by participant 2x having a personal measuring device 10x is illustrated in FIG. 1, and includes an audio-based presentation unit comprising earphones 14x. The earphones worn by participant 2x and may be connected to a receiving module (not shown) adapted for wirelessly receiving instructions 34 from the computer 22, or any other suitable communication for that matter (for example, processed data 32 transmitted from the device's communication means 16) in digital format, and converting it into audio signal to be transmitted to participant 2a. In this example, the personal device 10x may be attached to the earphones 14x as well, or alternatively may be attached to another body part of the participant 2x, for example the participant's wrist. In the latter example, the communication module 16 may have the ability to wireless transmit data D to the receiving module (not shown) that are connected to the earphones 14x. In another example, a presentation unit may be a single earphone that will operate in a similar manner to the earphones 14a described above.

It will be appreciated that the data D and/or instructions I may be presented to the participant in real-time, i.e. in the course of the activity and during the time the corresponding measurements are being taken.

It will also be appreciated, that a single participant may have more than a single presentation unit 14 as well as more than a single measuring device 10.

Alternatively, in yet another example, the presentation unit 14 may comprise a mechanism for providing signals that are configured to be felt by a body part including the skin, though optionally having no noticeable corresponding audio or visual effect. Such a mechanism may comprise, for example, a vibrating element that generates vibratory pulses and directs these to the skin of the participant 2 to enable the participant to feel the vibrations. Optionally, the frequency and/or amplitude of the vibrations may provide a measure of the data D and/or instructions I, according to a preset convention. For example, the more a particular parameter P of the particular body part to which the device 10 is attached deviates from a particular optimum, the higher the vibration frequency that is generated, enabling the participant to adjust his/her movements in a manner such that the vibrations subside. This particular form of presentation unit 14 enables the same to provide direct feedback information to the same part of the body as the device 10 which comprises the presentation unit 14 is fitted, and allows multiple units 10, fitted onto different body parts of the same participant 2, to simultaneously provide such information as required in a manner that is easily and readily understandable by the participant 2.

The Operation of the System—Example

Figure 8:
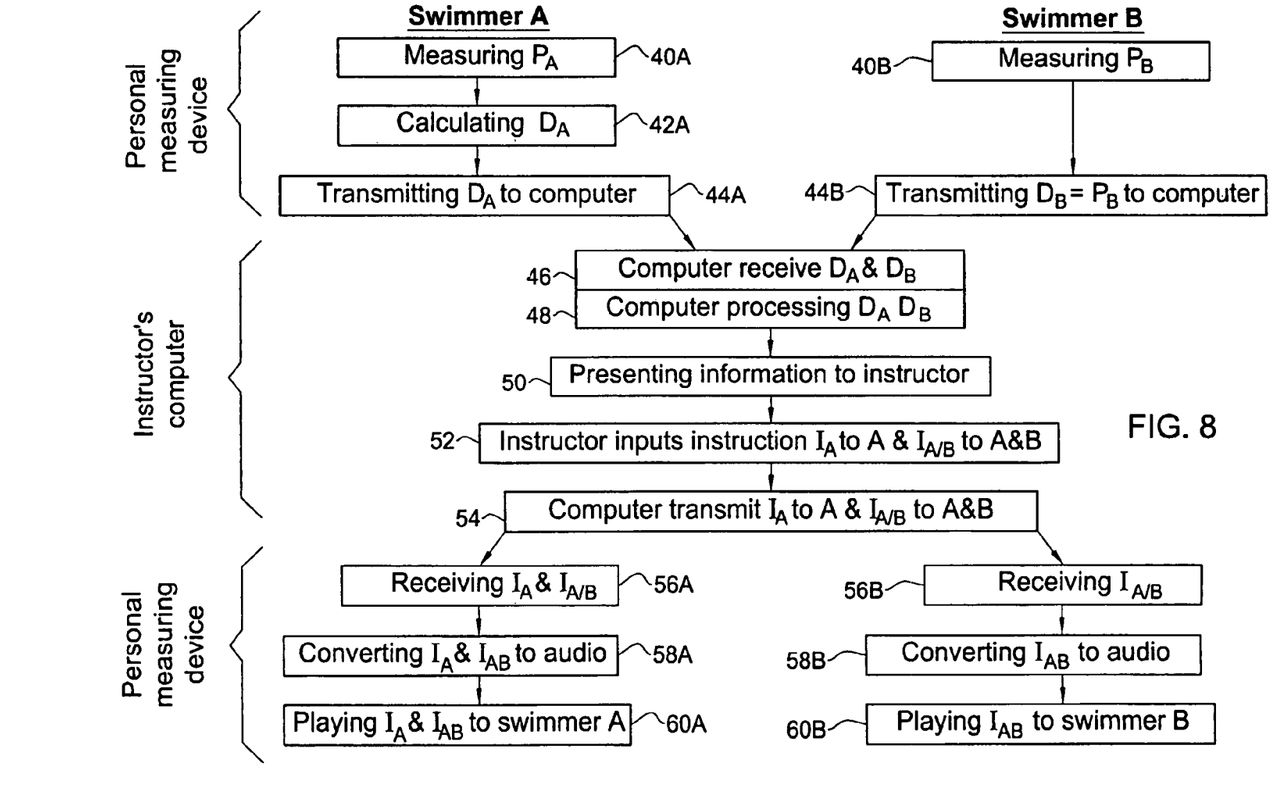
FIG. 8 is a flow chart diagram illustrating an example of operation of an advising system illustrated in FIG. 1 and using a sensing unit illustrated in FIG. 2.

FIG. 8 illustrates a flow chart diagram that describes an example operation of an advising system according to the embodiment of FIG. 1, and in which the activity is a swimming activity with two participants 2, swimmer A and swimmer B, and the instructor is a human instructor (i.e. not a virtual trainer). In this example, each swimmer A and B has a personal measuring device 10 which is attached to his wrist. The presentation unit 14 for each swimmer comprises earphones, and the sensing unit within each measuring device 10 is sensing unit 11 which is described above in accordance with FIGS. 2 and 4.

As swimmers A and B commence the swimming activity, each sensing unit 11 begins to take readings of the corresponding parameters $P_A$ and $P_B$ of the swimmers ($40_A$ and $40_B$ respectively), the obtained parameters including linear and angular acceleration values in this example and as described above. The measurement is performed repeatedly, the parameters being obtained by sampling measurements at every successive predetermined time interval. For each sampling, the measured values of parameter $P_A$ are transferred to processor 12 for further processing to enable calculation of the location and orientation of the wrist of the swimmer ($42_A$), which constitutes the data $D_A$, which is wireless transmitted to the instructor's computer 22 via the communication module 16 ($44_A$). In this example, the measured values relating to parameters $P_B$ are not processed in processor 12 and the unprocessed parameters $P_B$ constitute the data $D_B$ that is wireless transmitted to computer 22 via the communication module 16 ($44_B$).

Computer 22 receives both data $D_A$ and data $D_B$ (46), and further processes these data in order to generate the information as decided by the instructor 20 (48). This information can be any data which may be derived from the measuring devices of the swimmers as detailed above and exampled with reference to FIGS. 5-7. The computer 22, via its monitor 26, displays to the instructor 20 the generated information (50). The instructor 20, based on the displayed information, can then decide what instruction he/she would like to transmit to any of the swimmers A and B, and accordingly inserts this input, using input means 24, to the processor 23 of the computer 22 (52), to be subsequently transmitted to the swimmers (54). In this example, two streams of instructions I are transmitted: instruction $I_A$ is transmitted to swimmer A, and instruction $I_{AB}$ is transmitted to swimmer A and to swimmer B.

Each of the personal measuring devices 10 of the swimmers A and B receiving the instructions which are designated to them only, swimmer A receives instructions $I_A$ and $I_{AB}$ ($56_A$) and swimmer B receives instruction $I_{AB}$ ($56_B$). In this example, since both swimmers have earphones as presentation units 14, the instructions are received in the earphones' associated communication module as described above with reference to earphones 14x in FIG. 1 and converted to audio format ($58_A$ and $58_B$) to be played to each of the swimmers A and B, respectively ($60_A$ and $60_B$).

The Communication System

A closer look will be dedicated now to the communication with a participant in case the participant is a swimmer. The term "swimmer" used with reference to FIGS. 9 and 10 include any person engaged in water-related activities comprising one or more submerging periods characterized by natural communication barriers caused by submerging.

Figure 9:
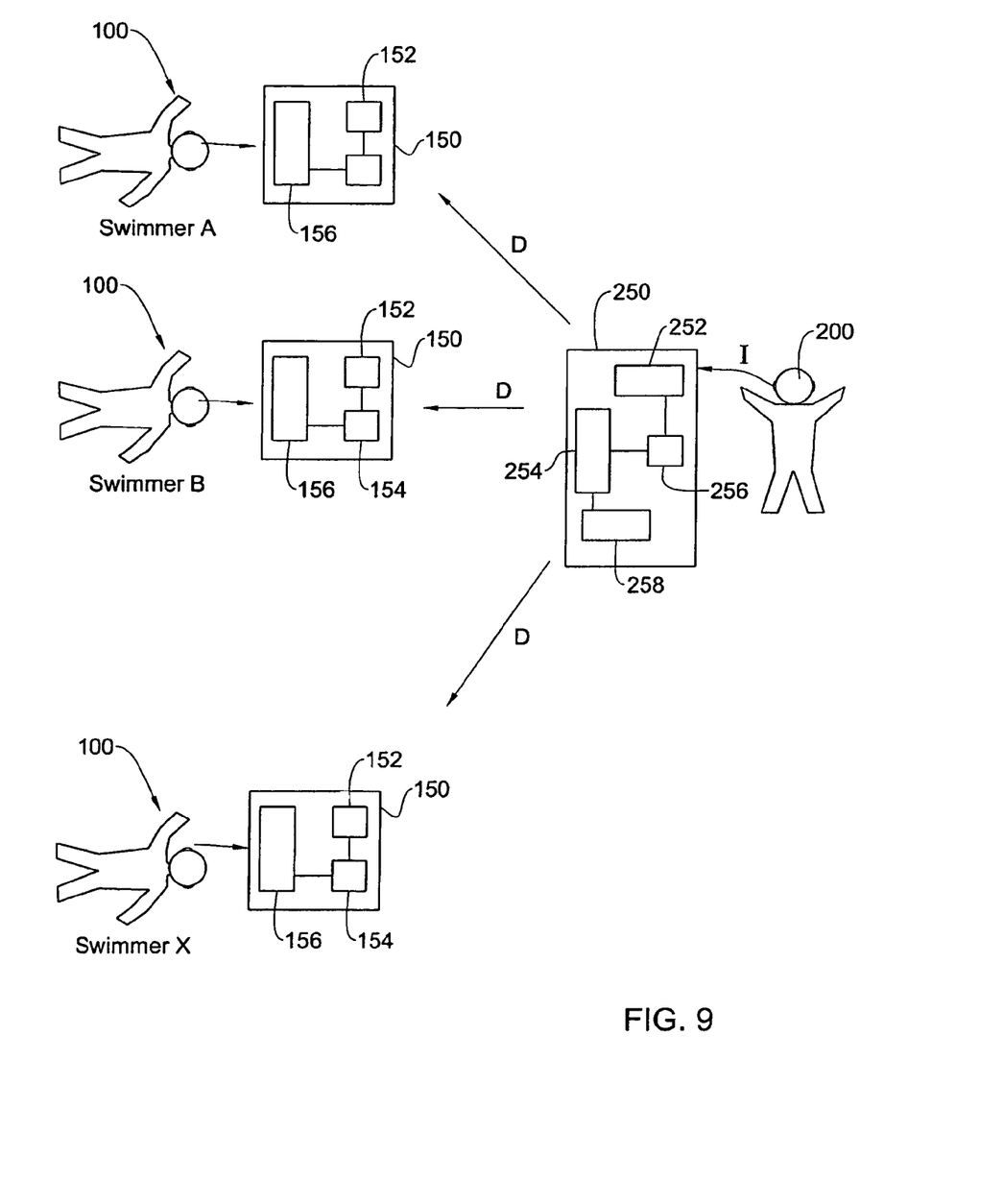
FIG. 9 is an illustration of a communication system according to still further embodiment of the present invention.

Reference is made now to FIG. 9 which illustrates a block diagram of a communication system for communicating with a certain swimmer or a group thereof. The communication system comprises a transmitting module 250 and one or more receiving modules 150, each associated with certain swimmer 100. The transmitting module 250 comprises an input unit adapted to obtain data designated to one or more certain swimmers or groups thereof (e.g. pre-recorded or obtained in real time training instructions I from an instructor 200, instructions generated by a "virtual trainer" in accordance with certain rules, messages designated to the swimmer, personalized music, etc.), a processor 254 connected to the input unit 252, storage/accommodating unit 256 connected to the processor 254 and communication module 258 connected to the processor and adapted to wirelessly transmit respective data D to one or more appropriate receiving modules 150. The input unit 252 may be, for example, a microphone, and in such a case, the transmitting module 150 will also include means (e.g. a vocoder, not shown) to convert the audio signal to digital format for processing. The transmitting module is adapted to obtain data designated to one or more swimmers or groups thereof, to accommodate said data and/or derivatives thereof (e.g. data in a digitalized and/or compressed form), to process (by the processor 254 and/or by the communication module 258) the accommodated data D or in order to fit it to certain wireless communication protocol, and to transmit the processed data to respective receiving module(s) upon a pre-defined condition. The predefined condition is communication availability of the respective receiving module(s); and the wireless communication protocol is configured to recognize communication availability of the respective receiving module(s). The wireless communication protocol may be, for example, a Bluetooth protocol or other appropriate protocol.

The computer 22 detailed with reference to FIG. 1 may comprise the transmitting module or parts thereof.

The receiving module 150 comprises a communication module 152 adapted to receive the data D transmitted by the transmitting module 250, a processor 154 adapted to process the data D received, and earphones 156 to present the data D in an audio format to the corresponding swimmer 100. The receiving module 150 may be attached to any of the swimmer's 100 ears, as well as to the headband of the swimmer's goggles (not shown). Earphones 156 can further present music or other types of audio data as well. In such a case, a digital media means adapted to present music, like an MP3 player, may be connected to receiving module 150 and/or to earphones 156. The receiving module 150 may also include a screen (not shown) to display the instructor's input to the swimmer 100.

Alternatively or additionally, receiving module 150 may be attached to the swimmer's wrist and may constitute part of another device (not shown), that can be a measuring device as described hereinabove, or a watch. It will be appreciated that a single system may include more than a single receiving module for one swimmer, as, for example, one receiving module will be attached to the swimmer's wrist, while the other one will be attached to the swimmer's head and be connected to earphones. In such example, both receiving modules may receive the transmitted data from the transmitting module 250 to be presented to the swimmer in various ways (e.g. using a screen and earphones, respectively), or in another example, only one of the receiving module can be adapted to receive the transmitted data from the transmitting module 250 and transmit it to the second receiving module.

In certain embodiments of the invention, the processor 254 may be adapted to compress the data D in order to enable transmission during a short period of time which is often shorter than the actual time in which the data D is received from the input unit 252 and/or displayed via the earphones 156 to the swimmer. For example, it may be desired to compress such data before the transmission when a duration of instructions designated to be heard by certain swimmer 100 is above a period of communication availability of the respective receiving device. In such embodiment, processor 154 at the receiving module may be adapted to decompress the received data in order to enable presenting the original data D to the swimmer 100 in an appropriate manner.

In certain embodiments of the invention, the transmission unit may be also configured to send the same or different data to several swimmers concurrently, in accordance with personal or group designation.

Those skilled in the art will readily appreciate that the invention is not bound by the configuration of FIG. 9; equivalent and/or modified functionality may be consolidated or divided in another manner and may be implemented in any combination of software, firmware and hardware.

Figure 10:
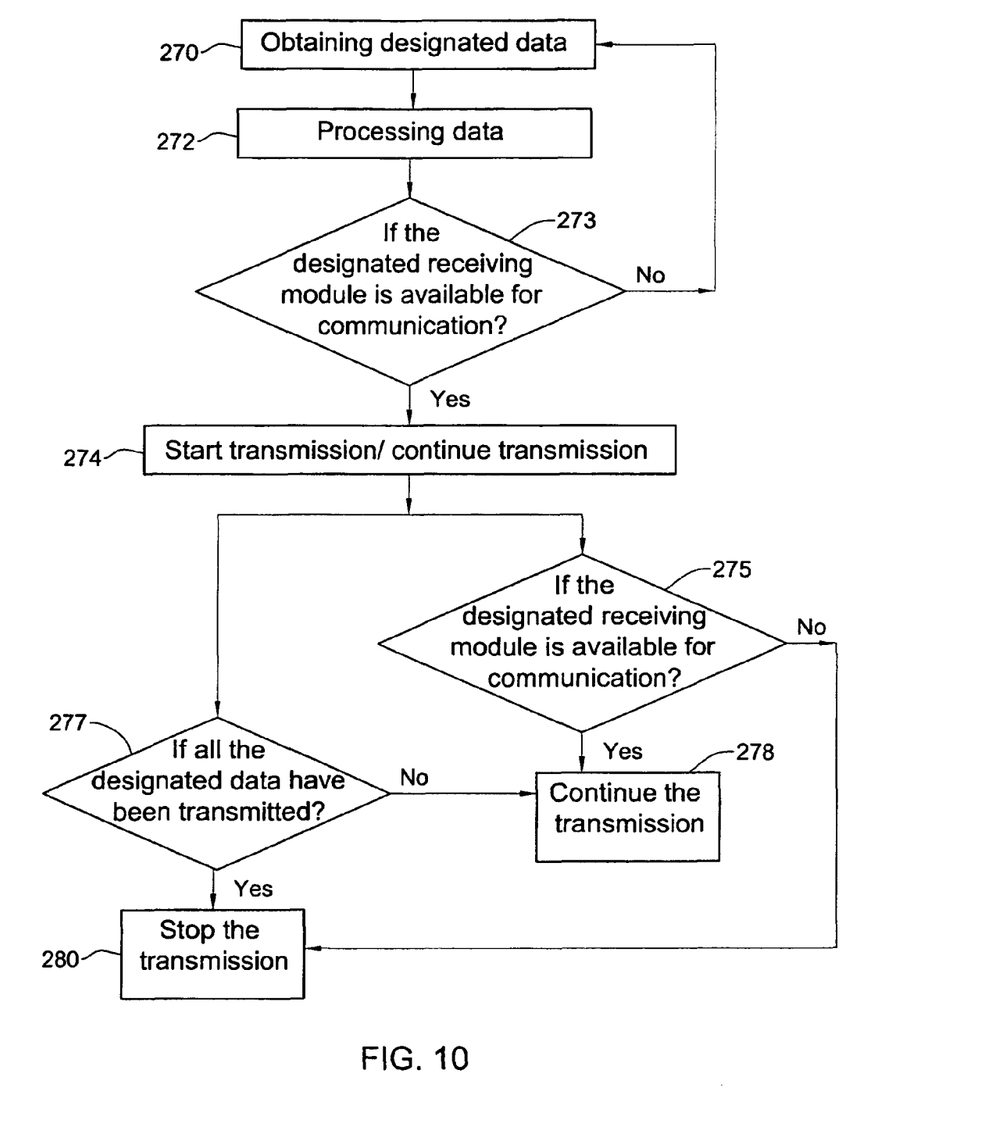
FIG. 10 is a flow chart diagram that describes a method of automated training in accordance with certain embodiments of the present invention.

Reference is made now to FIG. 10 which is a flow chart diagram that describes a method of automated training in accordance with certain embodiments of the present invention. The method may be implemented with a help of the communication system detailed with reference to FIG. 9, or otherwise.

The training starts with obtaining data (270) related to one or more training instructions designated to at least one swimmer among the swimmers.

In certain embodiments of the present invention, the transmitting module obtains that data from instructor 200, and the designated swimmer is swimmer A while there is plurality of other swimmers in the swimming pool, some of them having a receiving module 150. The obtained data may be recorded. The instructions may be based on input which the instructor receives concerning the swimmer's A movement. Such input may be based upon sensing devices which are attached to swimmer A. Alternatively, the data may be related to any other message or other information which the instructor wishes to transmit to one or more designated simmers or groups thereof. Also, an instructor may be a virtual trainer which is activated upon a pre-defined set of rules. In certain embodiments of the present invention the instructor 200 records his message by signaling the beginning and end thereof. The instructor also identifies to whom the message is designated. The identification may be made in various methods. One of which is stating out loud the name or number of the designated swimmer. In such a case means for converting audio (voice) into digital format (e.g. a vocoder, not shown) are required. Another method is pressing a key designating the identity of the swimmer. In any such method, the identification may be done before, during or after recording of the message. Accordingly, the message will be accommodated in the transmitting unit together with a digital mark, or other identifier, that indicates to whom the message is designated.

The obtained data is further processed (272) (e.g. by the transmitting module) in order to fit a wireless communication protocol (e.g. Bluetooth). The processing also may include other steps, which may occur in different order. In certain embodiments of the invention, the processing of the obtained data may include, for example, accommodating the data, converting an audio format to digital format data, exporting the data, manipulating the data according to predetermined rules, compressing the data and adding identification means (e.g. information bytes) to the data according to the designation of the recipient swimmer. The designated data may be accommodated in plurality of data blocks as to enable efficient transition thereof.

The wireless communication protocol is configured to facilitate recognition of communication availability of said at least one receiving module.

The transmission of the processed data to at least one receiving module associated with the swimmer A will start upon meeting (decision 273) a pre-defined condition. If such condition is not met, the transmission does not begin; optionally, additional data may be further obtained and added to the accommodated data awaiting transmission.

It will be appreciated that obtaining and processing the additional data may be provided respectless of the transmission process.

In this example, such a condition is the communication availability of at least one receiving device associated with the designated swimmer A. Communication availability means physical ability of communication between the transmitting module and the receiving module, this ability depends, for example, on a current submerging depth of the swimmer A. It should be noted that different availability criteria may be applied in different embodiments of the invention.

It will be appreciated that if receiving module 150 of swimmer A is either attached to his wrist or to his head, there will be frequent periods of times in which the receiving module will be out of the water, as swimmer A will have to strike his/her hand in order to swim and to raise his/her head above water in order to breathe. When the pre-defined condition, i.e. communication availability of swimmer A, is met, the data package is transmitted (274) to the receiving module 150 of swimmer A.

If all the designated data have been transmitted (decision 277, yes) or if the designated receiving device is no longer available to communicate (decision 275, no), for example, when the swimmer is underwater, then the transmission is stopped (280). Alternatively, if not all of the designated data have been transmitted yet (decision 277, no) and if the designated receiving module is available for communication (decision 275, yes) than the transmission is continued (278).

The transmitted data are receiving by one or more designated receiving units for further processing facilitating presentation of training instructions (or other information) to the respective swimmer.

In a certain embodiment of the present invention, the processing of the obtained data includes compression of the data before the transmission. For example, the compression rate may be adapted to enable a match between duration of the compressed instructions designated to certain swimmer and a period of communication availability of the respective receiving device. After receiving module 150, via communication module 152, receives the compressed data, the processor 154 decompresses the data which then may be presented to the swimmer A via earphones 156.

It should be noted that in certain embodiments of the invention, the transmission of the same or different data may be provided to several swimmers concurrently, in accordance with personal or group designation.

Those skilled in the art will readily appreciate that various modifications and changes can be applied to the embodiments of the invention as hereinbefore described without departing from its scope, defined in and by the appended claims.

The invention claimed is:

1. A personal device for measuring a training activity of a trainee having a body part which moves and changes its location and orientation, during said training activity, this movement at least partially defining said training activity, said device comprising:
   (a) a sensing unit adapted to repeatedly measure, during said training activity, parameters associated with the movement of said body part and characterizing the location and orientation of said body part relative to its initial location and orientation, and wherein said sensing unit comprising at least accelerometer means, a compass and optionally gyroscope means, said accelerometer means being adapted to measure linear acceleration of said body part along three axes, said gyroscope means being adapted to measure angular acceleration of said body part around said three axes, and said parameters being at least linear and angular acceleration values;
   (b) means for attaching the sensing unit to said body part; and
   (c) a processor adapted to receive from the sensing unit said parameters, and to calculate based thereon, data indicative of said training activity, said data including at least the location and orientation of said body part for ach of the measurements.

2. A device according to claim 1, wherein said activity is a swimming session and said data further includes statistics and summary results for said session.

3. A device according to claim 2, wherein said results include one or more of the following: total training time, number of laps, average lap time, average lap velocity, average strokes per lap, fastest and slowest lap, highest and lowest number of hand strokes per lap, instantaneous speed during the laps, hand or leg lifting height for each stroke, distance traveled for each stroke, comparative results to other trainees using similar devices.

4. A device according to claim 1, further adapted for infrared measurement of the pulse and wherein said data includes the pulse of the trainee.

5. A training advisor comprising a device according to claim 1, and further comprising a presentation unit adapted to present to the trainee at least said data or training instructions based on said data.

6. A training advisor according to claim 5, wherein said presentation unit comprises a screen connected to said processor and adapted for displaying to the trainee readings including at least said data or training instructions to the trainee based on said data.

7. A training advisor according to claim 5, wherein the processor of said device is further adapted to provide said training instructions according to predetermined rules.

8. A personal device for measuring a training activity of a trainee having a body part which moves during said training activity, this movement at least partially defining said training activity, said device comprising:
   (a) a sensing unit adapted to repeatedly measure, during said training activity, parameters associated with the movement of said body part, and wherein said sensing unit comprising at least accelerometer means, a compass and optionally gyroscope means;
   (b) means for attaching the sensing unit to said body part;
   (c) a processor adapted to receive from the sensing unit said parameters, and to calculate based thereon, data indicative of said training activity; and
   (d) at least one additional sensing unit and means for its attaching to an additional body part of said trainee, the sensing unit adapted to repeatedly measure, during said activity, parameters characterizing at least the location and orientation of said additional body part relative to its initial position and orientation; and said processor being further adapted to receive from said at least one additional sensing unit said parameters, and to calculate, based thereon, at least the location and orientation of said additional body part for each of the measurements, for use thereof in providing said data.

9. A personal device for measuring a training activity of a trainee having a body part which moves during said training activity, this movement at least partially defining said training activity, said device comprising:
   (a) a sensing unit adapted to repeatedly measure, during said training activity, parameters associated with the movement of said body part, and wherein said sensing unit comprising at least accelerometer means, a compass and optionally gyroscope means;
   (b) means for attaching the sensing unit to said body part comprising a flexible platform adapted to amplify at least one of the measurements performed by the sensing unit: and
   (c) a processor adapted to receive from the sensing unit said parameters, and to calculate based thereon, data indicative of said training activity.

10. A personal device for measuring a training activity of a trainee having a body part which moves during said training activity, this movement at least partially defining said training activity, said device comprising:
    (a) a sensing unit adapted to repeatedly measure, during said training activity, parameters associated with the movement of said body part, and wherein said sensing unit comprising at least accelerometer means, a compass and optionally gyroscope means;
    (b) means for attaching the sensing unit to said body part;
    (c) a processor adapted to receive from the sensing unit said parameters, and to calculate based thereon, data indicative of said training activity; and
    (d) a presentation unit adapted to present to the trainee at least said data or training instructions based on said data, said presentation unit comprising vibrating element adapted to generate vibratory pulses according to a predetermined rule, and to direct said pulses to the skin of said trainee.

11. A personal device for measuring a training activity of a trainee having a body part which moves during said training activity, this movement at least partially defining said training activity, said device comprising:
    (a) a sensing unit adapted to repeatedly measure, during said training activity, parameters associated with the movement of said body part, and wherein said sensing unit comprising at least accelerometer means, a compass and optionally gyroscope means;
    (b) means for attaching the sensing unit to said body part;
    (c) a processor adapted to receive from the sensing unit said parameters, and to calculate based thereon, data indicative of said training activity; and
    (d) a presentation unit adapted to present to the trainee at least said data or training instructions based on said data, said presentation unit comprising at least one earphone with a receiving module adapted for wirelessly receiving readings including at least the data from said device or training instructions to the trainee based on said data, and converting said readings into audio signal to be transmitted to the trainee via said at least one earphone.

12. A personal device for measuring a training activity of a trainee having a body part which moves during said training activity, this movement at least partially defining said training activity, said device comprising:
    (a) a sensing unit adapted to repeatedly measure, during said training activity, parameters associated with the movement of said body part, and wherein said sensing unit comprising at least accelerometer means, a compass and optionally gyroscope means;
    (b) means for attaching the sensing unit to said body part
    (c) a processor adapted to receive from the sensing unit said parameters, and to calculate based thereon, data indicative of said training activity;
    (d) a presentation unit adapted to present to the trainee at least said data or training instructions based on said data; and
    (e) a computer adapted for being located at a location spaced from said processor and for wirelessly receiving the data from said device, and having a monitor for displaying to a user of said computer said data or information derived therefrom.

13. A training advisor according to claim 12, wherein said computer further comprises an input unit to receive said training instructions from its user, the computer being adapted to wirelessly transfer said instructions directly or indirectly to said presentation unit.

14. A training advisor according to claim 12, constituting a part of a training system comprising a plurality of such training advisors for a corresponding plurality of trainees, and wherein said monitor is adapted to display to said user said data or information derived therefrom, relating to said plurality of trainees.

15. A training advisor according to claim 14, wherein said monitor is adapted to display to said user said data or information derived therefrom, in a real-time activity of said plurality of trainees.

16. A training advisor according to claim 14, wherein said computer further comprises an input unit to receive from its user the training instructions, the computer being adapted to simultaneously and wirelessly transfer said instructions directly or indirectly to each of said plurality of trainees.

* * * * *